US010363455B2

(12) United States Patent
Romero

(10) Patent No.: US 10,363,455 B2
(45) Date of Patent: Jul. 30, 2019

(54) EXERCISE MACHINE AND CROSS TRAINER

(71) Applicant: David L. Romero, Encinitas, CA (US)

(72) Inventor: David L. Romero, Encinitas, CA (US)

( * ) Notice: Subject to any disclaimer, the term of this patent is extended or adjusted under 35 U.S.C. 154(b) by 78 days.

(21) Appl. No.: 15/696,060

(22) Filed: Sep. 5, 2017

(65) Prior Publication Data

US 2019/0070463 A1    Mar. 7, 2019

(51) Int. Cl.
*A63B 23/035* (2006.01)
*A63B 21/00* (2006.01)
(Continued)

(52) U.S. Cl.
CPC .......... *A63B 26/00* (2013.01); *A63B 21/0552* (2013.01); *A63B 21/063* (2015.10); *A63B 21/0724* (2013.01); *A63B 21/154* (2013.01); *A63B 21/16* (2013.01); *A63B 21/4034* (2015.10); *A63B 21/4035* (2015.10); *A63B 21/4043* (2015.10); *A63B 22/0002* (2013.01); *A63B 22/02* (2013.01); *A63B 22/0605* (2013.01); *A63B 22/0664* (2013.01);
(Continued)

(58) Field of Classification Search
CPC .............. A63B 21/0552; A63B 21/063; A63B 21/0724; A63B 21/154; A63B 21/16; A63B 21/4034; A63B 21/4035; A63B 21/4043; A63B 22/0002; A63B 22/02; A63B 22/0605; A63B 22/0664; A63B 23/0355; A63B 23/03558; A63B 23/03575; A63B 24/0075; A63B 26/00; A63B 2022/0652; A63B 2208/0233; A63B 2208/0238
See application file for complete search history.

(56) References Cited

U.S. PATENT DOCUMENTS 4,463,945 A    8/1984 Spector
4,625,962 A  * 12/1986 Street ................... A63B 21/015
                                                    482/116
(Continued)

*Primary Examiner* — Joshua Lee
(74) *Attorney, Agent, or Firm* — Law Office of David L Romero

(57) ABSTRACT

The present invention is directed, in part, to a system and methods for combining newly designed cardiovascular equipment with the added features of an upper body weight training regimen in order to provide a user a full body workout, cardiovascular exercise and weight training simultaneously. The invention does so by employing either a weight tray apparatus configured to newly designed cardiovascular equipment or machine or through the use of an adjustable weight training apparatus combined with the newly designed cardiovascular equipment or machine. More specifically, the present invention relates to a system and methods for combining newly designed cardiovascular equipment including stationary and recumbent bikes, elliptical machines, treadmills and stair steppers, with a tray apparatus that allows a user to employ free weights. The invention further relates to a system and methods for combining newly designed cardiovascular equipment including stationary and recumbent bikes, elliptical machines, treadmills and stair steppers that are configured with an adjustable weight training apparatus that allows a user to build upper body muscle groups simultaneously with cardiovascular exercise, in effect, providing a full body workout.

20 Claims, 7 Drawing Sheets

(51) Int. Cl.
*A63B 21/16* (2006.01)
*A63B 22/00* (2006.01)
*A63B 22/02* (2006.01)
*A63B 22/06* (2006.01)
*A63B 24/00* (2006.01)
*A63B 26/00* (2006.01)
*A63B 21/055* (2006.01)
*A63B 21/062* (2006.01)
*A63B 21/072* (2006.01)

(52) U.S. Cl.
CPC .... *A63B 23/03575* (2013.01); *A63B 24/0075* (2013.01); *A63B 2022/0652* (2013.01); *A63B 2208/0233* (2013.01); *A63B 2208/0238* (2013.01)

(56) References Cited

U.S. PATENT DOCUMENTS

| | | | |
|---|---|---|---|
| 5,044,627 A | 9/1991 | Huang | |
| 5,480,366 A | 1/1996 | Harnden | |
| 5,951,449 A * | 9/1999 | Oppriecht | A63B 21/0087 482/103 |
| 6,902,515 B2 * | 6/2005 | Howell | A63B 22/0012 482/57 |
| 7,427,257 B1 * | 9/2008 | Chernet | A63B 21/0615 482/142 |
| 8,025,607 B2 | 9/2011 | Ranky | |
| 9,545,540 B1 * | 1/2017 | Moschel | A63B 22/0046 |
| 9,737,760 B2 * | 8/2017 | Harrer | A63B 21/0552 |
| 9,878,201 B1 * | 1/2018 | Moschel | A63B 22/0012 |
| 9,919,183 B1 * | 3/2018 | Moschel | A63B 22/0605 |
| 10,149,999 B2 * | 12/2018 | Moschel | A63B 22/0605 |
| 2004/0043873 A1 * | 3/2004 | Wilkinson | A63B 21/015 482/54 |
| 2004/0082443 A1 * | 4/2004 | Britt | A63B 21/154 482/94 |
| 2006/0019804 A1 * | 1/2006 | Young | A63B 21/154 482/93 |
| 2006/0135322 A1 * | 6/2006 | Rocker | A63B 23/1209 482/54 |
| 2009/0118103 A1 * | 5/2009 | Ellis | A63B 21/00076 482/54 |
| 2011/0082009 A1 | 4/2011 | Ranky | |
| 2011/0118089 A1 * | 5/2011 | Ellis | A63B 21/155 482/54 |
| 2011/0172064 A1 * | 7/2011 | Cutler | A63B 21/0552 482/63 |
| 2011/0251020 A1 * | 10/2011 | Caragio | A63B 21/0056 482/5 |
| 2011/0281691 A1 * | 11/2011 | Ellis | A63B 22/0012 482/54 |
| 2013/0281271 A1 * | 10/2013 | Nizam | A63B 23/03558 482/139 |
| 2013/0310222 A1 | 11/2013 | Wray | |
| 2014/0364281 A1 * | 12/2014 | Moschel | A63B 21/00047 482/80 |
| 2014/0364282 A1 * | 12/2014 | Moschel | A63B 22/0605 482/80 |
| 2017/0080320 A1 | 3/2017 | Smith | |
| 2017/0266503 A1 * | 9/2017 | Watterson | A63B 21/0726 |
| 2017/0326411 A1 * | 11/2017 | Watterson | A63B 21/072 |

* cited by examiner

EXERCISE MACHINE AND CROSS TRAINER

FIELD OF THE INVENTION

The present invention relates generally to a system and methods for cardiovascular exercise and weight training. More particular, the invention provides for a device that combines the cardiovascular exercise of an elliptical, treadmill, stationary or recumbent bike with the added benefit of simultaneous weight training.

BACKGROUND OF THE INVENTION

Newly designed cardiovascular equipment including for example, treadmills, elliptical machines and stationary and recumbent bikes provide a user with the benefits of a exercising the individual's heart, lungs and other parts of the body with increased oxygen distribution and endurance. Contrary, a weight training regimen provides the individual with increased strength, muscle definition and body toning and sculpting. Under most circumstances however, cardiovascular equipment does little to increase the overall strength of an individual and likewise, weight training does little to increase exercise to the heart, lungs or to increase the individual's overall endurance for sustained exercise.

In light of the current state of the art therefore, there is an overall lack of exercise equipment that provides an individual with a cardiovascular workout and a weight training exercise regimen simultaneously, all in a stationary platform apparatus.

In that regard, various solutions in the art have arisen in order to address the need for a system and methods that both increase cardiovascular activity as well as increase strength through weight training.

To that end, various systems have come about in the form of cross training equipment to provide the average consumer with options in achieving the individual's fitness goals. The present invention goes beyond that which is known in the prior art by allowing individuals the ability to obtain both a cardiovascular workout as well as a weight training capability, all on a single system, simultaneously.

In reference to the current state of the art the differences between cardiovascular exercise equipment and strength and weight training equipment are significant. For example, generally speaking an individual exercising on a stationary bike typically sits on a bike seat while peddling. Cardiovascular exercise is pronounced however, strength and weight training is nominal and limited solely to the legs. Moreover, this nominal strength training focuses exercise on a single muscle group only, leaving the other muscles groups of the upper body idle during the individual's time on the bike.

Likewise, when walking on a treadmill, a user enjoys the benefit of cardiovascular exercise however with the exception of legs, again, a single muscle group, there is no significant weight training. The individual's other muscle groups are left with no weight training regimen for the entire period of time the individual walks on the treadmill.

Similarly, elliptical machines provide excellent cardiovascular exercise however again, upper body muscle groups are left without any weight training exercise during the entire time on the machine. For an individual who exercises for 30 minutes a day on an elliptical machine, this amounts to 3.5 hours of exercise time per week that an individual misses the opportunity to exercise upper body muscle groups.

In today's fast paced and ultra-busy day, individuals who exercise routinely strive for efficient ways of incorporating an effective exercise regimen which also works within the time constraints of their day.

SUMMARY OF THE INVENTION

The present invention is directed to an improved method and a system that provides an overall full body workout by providing a cardiovascular workout in combination with a weight training regimen simultaneously. Cardiovascular exercise is provided by employing an improved stationary or recumbent exercise bike platform, or through use of a modified and improved treadmill or stair stepper apparatus. These exercise platforms are combined with a weight training apparatus to provide an upper body weight training exercise workout simultaneously through the use of either free weights that are employed with attached trays or alternatively, through the use of weight training apparatus that is combined and attached to the cardiovascular equipment being used.

In particular, the present invention combines a newly designed stationary bike with a tray apparatus that allows a user to utilize free weights simultaneously while engaging in cardiovascular exercise on the stationary bike. The present invention also includes a recumbent stationary bike with a tray apparatus that allows a user to employ use of free weights simultaneously during cardiovascular exercise on the recumbent bike. The present invention further includes a newly designed stair stepper apparatus in combination with a tray apparatus so that an individual can employ use of free weights during the course of stair stepping exercise. The present invention further includes a newly designed treadmill apparatus in combination with a tray apparatus that allows an individual to employ free weights during treadmill exercise. The present invention further provides a newly designed elliptical machine in combination with a tray apparatus wherein the user employs use of free weights during the course of exercising on the elliptical.

The present invention further includes a newly designed stationary bike apparatus combined with weight training equipment that is configured to be attached to the stationary bike. In particular, the weight training equipment is configured on the stationary bike so that a user is able to weight train upper body muscle groups during stationary bike and cardiovascular exercise.

Likewise, the invention also includes other newly designed cardiovascular equipment such as for example, a recumbent bike, an elliptical machine, a stair stepper and a treadmill, all of which are configured and combined with weight training apparatus to provide a user with both a cardiovascular workout as well as a upper body weight training regimen simultaneously, in essence providing a full body workout all in one single piece of cross training exercise equipment.

In particular, The exercise system and method of the invention provides an exercise system to provide a full body cardiovascular and upper body work out that includes at least one piece of adjustable weight training apparatus; a mountable cardiovascular machine; wherein the at least one piece of adjustable weight training machine is configured with and directly connected to the mountable cardiovascular machine; wherein the adjustable weight training apparatus comprises, support equipment, resistance cables, cable pulleys, weight handles and weight plates wherein the weight training apparatus is adjusted by a user whom has mounted the mountable cardiovascular machine; wherein the user adjusts the amount of weight the user desires to undertake in upper body exercise by selecting the number of weight plates the user desires; wherein the adjustable weight training apparatus is adjusted by the user so that the apparatus is positioned over the user's head, at a midway position or in a lowered position; wherein the exercise system apparatus further comprises weight trays designed to hold at least two free weights; wherein the weight trays are configured in the front section of the mountable cardiovascular machine in front of the user within reach of the user; wherein weight trays are also attached to the mountable cardiovascular machine and positioned on both sides of the user within reach of the user; wherein the exercise system further comprises an "app" uploaded onto a smart or mobile device; wherein the "app" provides the user with a rate that the user engages in cardiovascular exercise and also directs the user as to the upper body exercises to be undertaken using the adjustable weight training apparatus; wherein the user engages in cardiovascular exercise while simultaneously engaging in upper body weight training thereby engaging in a full body workout including both cardiovascular and upper body exercise The exercise system and method of the invention allows the user engages in arm and shoulder pull down exercises at times when the adjustable weight training apparatus is positioned over the user's head.

The exercise system and method of the invention allows the user to engage in pectoral and chest exercises at times when the adjustable weight training apparatus is positioned at the midway position.

The exercise system and method of the invention allows the user to engage in arm pull up exercises at times when the adjustable weight training apparatus is positioned in a lowered position.

The exercise system and method of the invention includes a mountable cardiovascular machine that is an upright stationary bike.

The exercise system and method of the invention includes a mountable cardiovascular machine that is a recumbent stationary bike.

The exercise system and method of the invention includes a mountable cardiovascular machine that is a treadmill.

The exercise system and method of the invention includes a mountable cardiovascular machine that is an elliptical machine.

The exercise system and method of the invention includes weight trays configured in front of the user configured into the front panel or handle bar of the mountable cardiovascular machine.

The exercise system and method of the invention allows a user to perform various upper exercises by lifting the free weights.

The exercise system and method of the invention also allows a user to continuously exercise the user's lower body by engaging the mountable cardiovascular machine during periods of time when the user is not conducting upper body exercises with the free weights, the free weights being placed in the weight trays

DETAILED DESCRIPTION OF THE INVENTION

Figure 1:
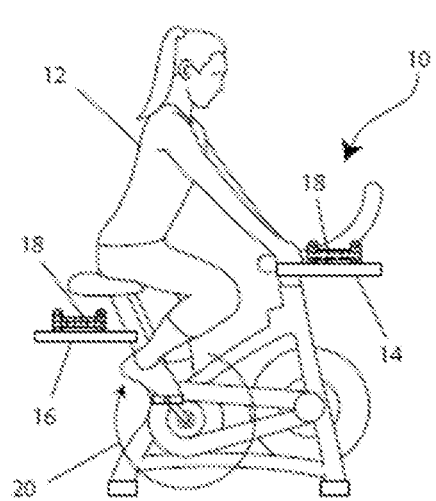
FIG. 1 depicts a preferred embodiment of the invention. In particular, a newly designed stationary bike is shown configured with a tray apparatus wherein a user employs use of free weights during cardiovascular exercise on the bike. Weights are shown placed within trays configured in front of and on either side of a user so that the user is able to easily reach the weights while maintaining cycling on the bike.

The present invention provides a system, system app and methods that efficiently and accurately allow users to combine the beneficial health effects of cardiovascular exercise with upper body weight training. As described herein weight training is provided with a set of trays configured and attached to the cardiovascular equipment, the trays designed to hold free weights in close proximity (i.e., either in front of, or on either side of a user) to the user during cardiovascular exercise. In such a configuration, the user can conduct weight lifting "sets" with free weights and in between sets, is able to rest the weights in the trays while maintaining cardiovascular exercise both during and in between weight lifting sets. In so doing, the invention provides the user with a full body workout.

Alternatively, the invention further provides a full body work out employing newly designed cardiovascular equipment configured with a weight training apparatus that includes adjustable weight plates so that each individual can adjust the appropriate weight for that particular individual, either higher weight or lower, depending on the user's capabilities. As described herein, the weight training apparatus of the invention includes cables and plate weights designed with a pulley system so that a user can access the weight training apparatus and hand holds of the apparatus during continued cardiovascular exercise.

The weight apparatus of the invention is designed to be adjustable to perform different weight training exercises including for example, curls, shoulder presses, triceps exercises, pectoral and chest presses as well as a variety of other upper body weight training exercises. As described, the invention is designed to allow a user to use the weight training apparatus simultaneously with cardiovascular exercise on the cardiovascular equipment that is configured with the weight training apparatus.

The system and methods of the invention include newly designed cardiovascular equipment such as for example, upright and recumbent stationary bikes, elliptical machines, treadmills and stair steppers. Other cardiovascular equipment not mentioned expressly herein is also envisioned and within the scope of the invention.

A preferred embodiment of the invention includes newly designed cardiovascular equipment similar to an upright or recumbent stationary bike, elliptical machine, stair stepping machine or a treadmill configured with weight holding trays designed to hold free weights that can be easily accessed by a user engaged in exercise activity on the cardiovascular equipment. The user is able to undertake cardiovascular exercise while also undertaking upper body weight training with free weights to provide a full body workout. An "app" of the invention is designed to provide a user with workout routines that include both cardiovascular routines as well as various weight lifting sets that are performed simultaneously on the invention.

In another related embodiment, the trays are configured and attached to the front and sides of a recumbent bike so that a user is easily able to access free weights placed within the trays. In a related embodiment, the trays are configured and attached to a treadmill in front of and on either side of a user engaged in treadmill activity. In yet another related embodiment, the trays are configured and attached to a stair stepper with trays situated in front of and on either side of the user so that the user can easily access the free weights therein. In another related embodiment, the invention provides trays configured and attached to an elliptical machine wherein the trays are situated in front of, and on either side of the user so that free weights can be used during elliptical activity. Also envisioned are other forms of cardiovascular equipment not expressly described herein but within the purview of the art.

In yet another preferred embodiment, the invention includes newly designed cardiovascular equipment (for example, upright and recumbent stationary bikes, treadmills, elliptical machines and stair steppers, and the like) configured with weight training apparatus attached to the cardiovascular equipment in such a way that allows a user to undertake upper body weight training simultaneously with cardiovascular activity. As described herein, the weight training apparatus is designed to be adjustable to so that a user can undertake a variety of weight training and upper body exercises during the course of cardiovascular activity.

In yet another embodiment of the invention the weight training apparatus is configured onto a piece of cardiovascular equipment that is a recumbent stationary bike. A further element of the invention includes use of an "app" that provides a user with weight training instructions so that the user can undertake several "sets" of weight lifting during, and simultaneous to, the cardiovascular exercise, in order to give the user a full body workout. Use of the app also provides the user with the ability to moderate and adjust the weight training regimen either to be more intense, or less, depending on the capability of the user.

The term "mountable cardiovascular machine" as used herein includes any cardiovascular machine as generally known in the art including but not limited to stationary and recumbent bikes, elliptical machines, treadmills, stair steppers and any other cardiovascular machine that is amenable to attachment and configuration with the adjustable weight training apparatus as described herein.

The term "support equipment" as used herein generally refers to the hardware employed as the mechanism for pulleys, weight cables, weight handles and the like. For example, support equipment of the invention includes but is not limited to hardware that connects the adjustable weight apparatus to the mountable cardiovascular machine and may include all metal types and any other materials that can be employed in attached the elements of the invention to one another.

The term "weight handles" as used herein generally refers to the grips from which a user grasps during instances in which the user engages in upper body exercises conducted using the adjustable weight apparatus.

The terms "over the user's head", "midway position" and "lowered position" as used herein generally refer to the following;

The term "rate", "cardiovascular rate" and the like as used herein generally refers to the degree of cardiovascular exercises undertaken by a user. For example, a user exercising on a stationary bike can increase his rate by increasing the number of revolutions per minute from 50 to 90. Likewise, a user can increase his weight lifting repetitions from 10 to 20 per set.

The term "sets", "set" and the like as used herein generally refers to upper body exercises conducted by the user when using either the adjustable weight apparatus of the invention or alternatively, when lifting free weights while engaging the cardiovascular machine. For example, a user will undertake 3 sets of 10 repetitions when that user performs 10 repetitions of weight lifting for a total of three times with periods of rest between each set of repetitions. The term "sets" as intended herein is defined as is generally known in the art of weight lifting.

The term "upper body exercises" and the like as used herein generally includes reference to all upper body exercises as generally known in the art. For example, upper body exercise can include curls and other upper body exercises as known in the art.

The term "arm pulls", "shoulder pulls" and the like as used herein generally refer to all upper body exercises as generally known in the art that exercise the arms and shoulders.

The term "chest exercises", "pectoral exercises" and the like as used herein generally refer to all upper body exercises as generally known in the art that exercise the chest muscles.

The term "pull up", "pull up exercises" and the like, as used herein refers generally to exercises known in the art such as for example, curls and arm pull ups.

The term "front panel" and the like as used herein generally refers to the front portion of a cardiovascular machine which generally includes a video screen or hand grips. For example, a front panel of the invention is provided in the illustrations, specifically FIG. 16, reference 52 provides an example of a front panel.

The term "handle bar" and the like as used herein, generally refers to the front portion of a cardiovascular machine which generally includes a video screen or hand grips. For example, the handle bar of the invention is provided in the illustrations, specifically FIG. 16, reference 50 provides an example of a handle bar.

Turning now to the substance of FIGS. 1 to 16 and the preferred embodiments of the invention.

Figure 16:
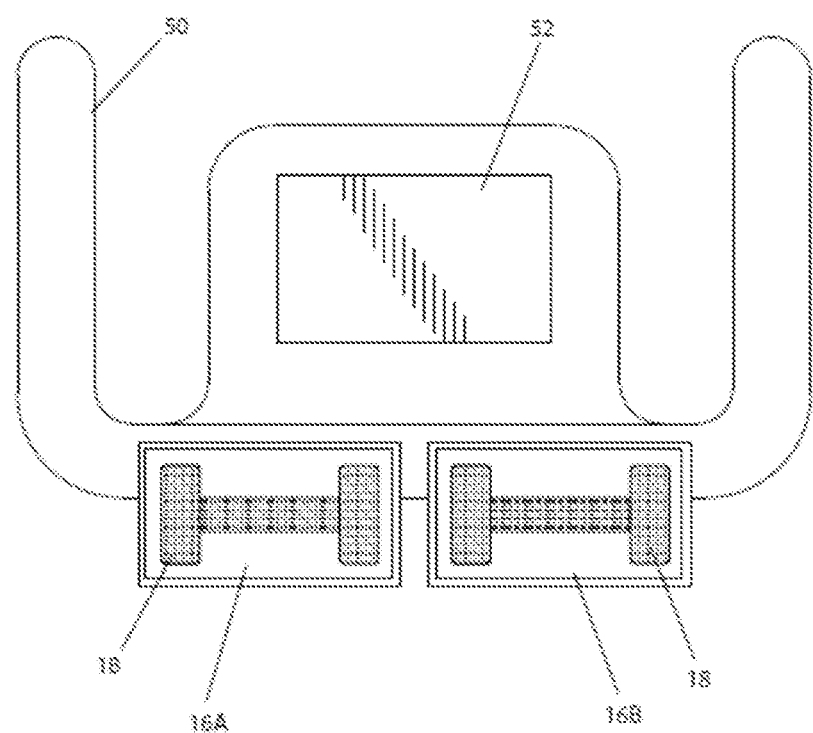
FIG. 16 illustrates another preferred embodiment of the weight trays embodiment in which the weight trays are configured on the front of the stationary bike on the handle bar. In this configuration a user will grasp weights placed in the weight trays as he would a typical handle bar. During periods of weight lifting sets, the user can lift the weights out of the weight trays and engage in weight training exercise simultaneously with cardiovascular exercise.

FIG. 1 illustrates a preferred embodiment of the invention 10 employing use of weight trays. In particular, a rider 12 is shown riding a newly designed stationary bike while peddling 20. In the embodiment the stationary bike is configured with weight trays 14, 16 in two or more areas of the bike. As shown, weight trays are located at the front of the stationary bike 14 in two specific orientations with weights 18 located on the trays. The first, as shown in FIG. 1 in a configuration perpendicular to the handle bar and the second, as shown in FIG. 16 (16A, 16B) configured parallel to the handle bar. In the second configuration, the trays and weights are used as a part of the handle bar allowing the user to grasp the weights while the weights 18 are not used and between weight lifting sets. FIG. 1 illustrates the rider peddling on the stationary bike between weight lifting sets. As such the weights are placed in the trays until such time that the user wishes to begin a weight lifting set.

Figure 2:
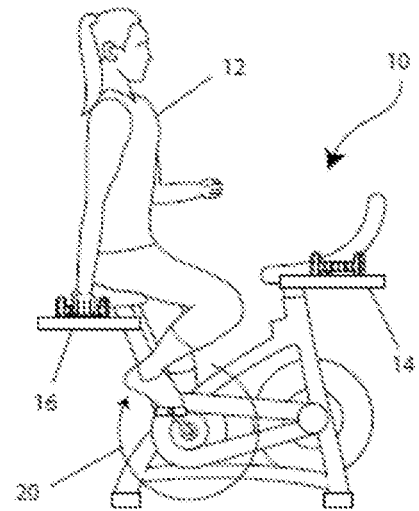
FIG. 2 illustrates a user riding a newly designed stationary bike configured with a tray apparatus, with trays located in front of and on either side of a rider/user. In particular the illustration depicts the user reaching for and accessing a free weight that has been placed on one of the trays so that the user is able to perform several sets of curls or shoulder lifts during riding. The trays allows the user to place the weights back onto the trays between sets.

FIG. 2 illustrates the weight trays embodiment of the invention 10 where in a user 12 is peddling on a newly designed stationary bike 10. As shown, portable free weight dumb bells 18 are placed in weight trays configured at the front of the bike 14 and on either side of the rider 16. In the Figure, the user is grasping one of the weights in preparation of beginning a weight training set.

Figure 3:
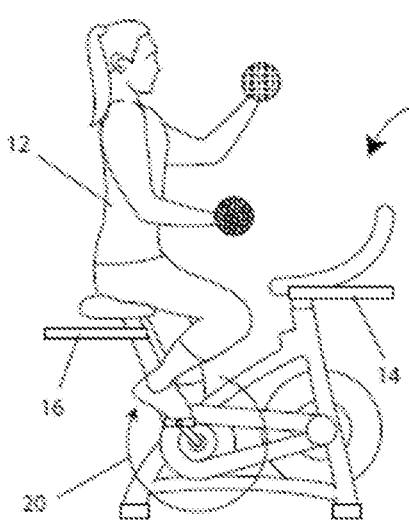
FIG. 3 depicts a user/rider in course of doing a set of curl exercises on the stationary bike configured with trays. In particular, the illustration shows a user lifting free weights in the course of also riding a stationary bike. Once the user has completed a set, of 10 curls for example, the user places the free weights back onto the trays until such time that the user wishes to do another set of curls. Throughout the time the user does several sets, the user continues to ride the stationary bike to maintain cardiovascular exercise and to keep heart rate elevated for maximum health benefit.
Figure 4:
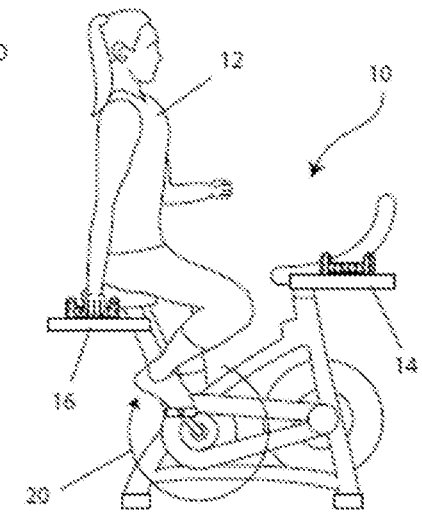
FIG. 4 illustrates a user whom has completed a set of curls or shoulder exercises while riding a stationary bike configured with trays. As shown, the user places the free weight onto the trays configured on the tray adjacent to the user after completing a set of curls or shoulder exercises using the free weight.

FIG. 3 illustrates a preferred embodiment of the newly designed stationary bike 10 wherein the user 12 is actively engaged in both weight training and cardiovascular exercise simultaneously. As shown, the user has lifted the free weights out of the weight trays 14, 16 while peddling 20 and is actively engaged in a set of curls. FIG. 4 illustrates the user 12 wherein the user has completed a weight training set and has placed the free weights back into the weight trays 14, 16 however, continues to peddle ensuring that a high heart rate is maintained even between weight sets.

FIGS. 5 through 14 illustrate yet another preferred embodiment of the newly designed stationary bike in which an adjustable weight training apparatus has been attached to the stationary bike. It is noted that the adjustable, weight training apparatus provided in the Figures are not limited to only upright stationary bikes but are also envisioned for use with recumbent stationary bikes, elliptical machines, stair steppers, treadmills as well as any other piece of cardiovascular equipment that is amendable to incorporation of the weight training apparatus, as known in the art.

Figures 5, 6:
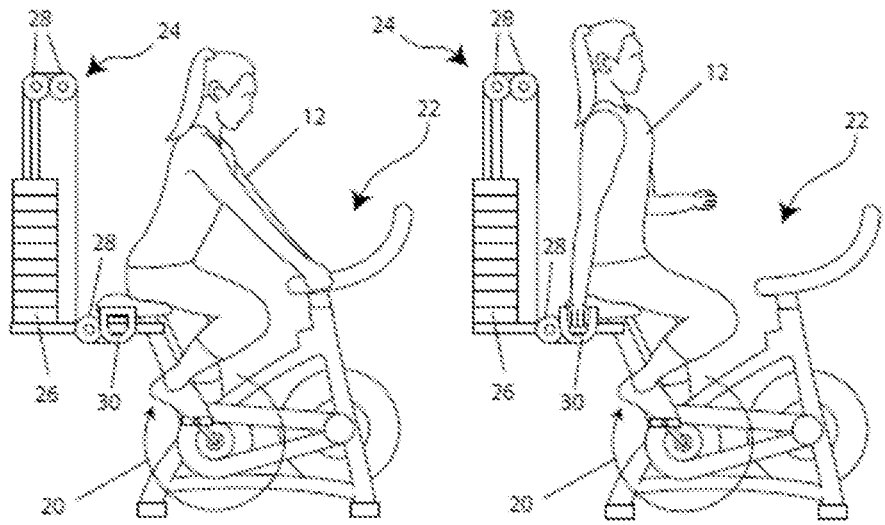
FIG. 5 illustrates a newly designed stationary bike configured with an attached weight training apparatus. In particular, the figure depicts a user in the course of riding a stationary bike for cardiovascular exercise. Attached to the stationary bike is a weight training apparatus configured with a set of adjustable weight plates. As envisioned, the weight plates can be replaced with weight stretch bands.
FIG. 6 depicts a user riding a newly designed stationary bike with an attached weight training apparatus. In particular, while riding the bike, the user is able to easily reach and grasp a hand grip configured on the weight training apparatus in order to begin a set of exercises that may include for example, curls, shoulder pulls, triceps extensions, among others, while simultaneously continuing cardiovascular exercise on the bike.

In particular, FIG. 5 illustrates a newly designed stationary bike 22 wherein an adjustable weight training apparatus 24 is combined with the bike. The weight training apparatus allows a user 12 to adjust the weight training apparatus in two ways. First, the user adjusts the amount of weight plates 26 that is appropriate for the user. Second, the user can adjust the weight training apparatus so that the handles 30 and pulley system 28 are in a low position or in an overhead position. FIG. 5 shows the weight training apparatus 24 wherein handles are in the lower position which allow the user to engage in arm curls and shoulder pull ups as well as any other weight training as known in the art. As discussed, the user peddles continuously 20 while either engaged in weight training exercise or not.

Figures 7, 8:
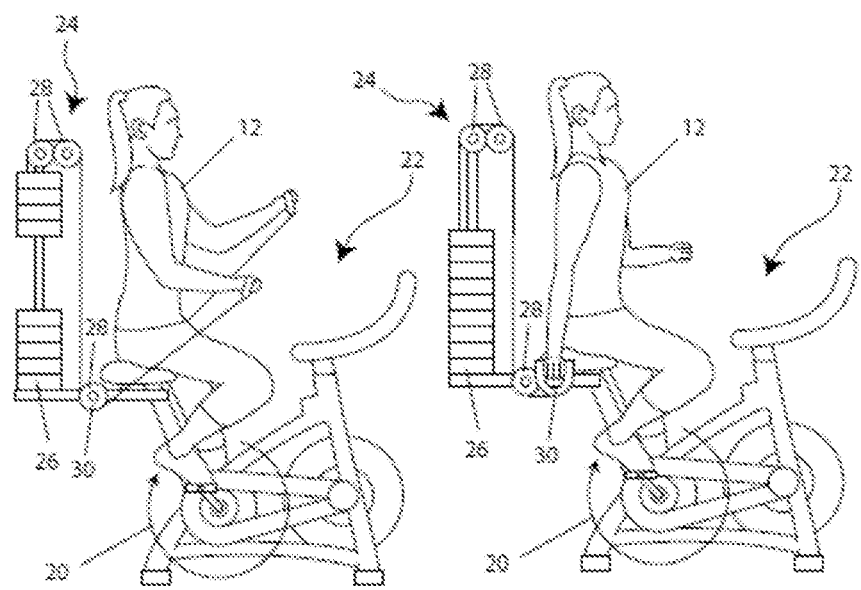
FIG. 7 depicts a user riding stationary bike while also doing a set of curl exercises. In particular, a user is doing a set of curls using the attached configured adjustable weight training apparatus wherein the user has grasped hand holds that are connected to weight plates via a cable and pulley system.
FIG. 8 illustrates a user riding a stationary bike configured with an attached weight training apparatus fitted with weight plates, wherein the user is able to adjust the number of weight plates to be employed during exercise. In particular, the user is depicted releasing the hand hold after completing a set of exercises for example, curls, should pulls or triceps exercises. As shown, throughout the time the user is doing a set of upper body weight training exercises, cardiovascular exercise on the bike is maintained and continued in order to keep heart rate elevated and provide maximal health benefit.

FIG. 6 illustrates the newly designed stationary bike preferred embodiment 22 wherein a user 12 is preparing to begin a weight training set by grasping a weight handle 30. The user has adjusted the amount of weight appropriate for the user by selecting an appropriate amount of weight plates 26. As shown, the adjustable weight training apparatus has been adjusted to occupy a low position for lifting weight training. FIG. 7 illustrates a user actively engaged in upper body arm curls using the weight training apparatus while actively engaging in cardiovascular peddling 20. As can be seen in the Figure, the user has lifted 4 weight plates 26 using the pulley system 28 of the adjustable weight training apparatus 24. FIG. 8 illustrates a user 12 whom has concluded a weight training set on the newly designed stationary bike 22 configured with an adjustable weight training apparatus. In the illustration, the user is lowering the handle 30 to its initial starting point and allowing the weight plates 26 back into their initial position.

Figure 9:
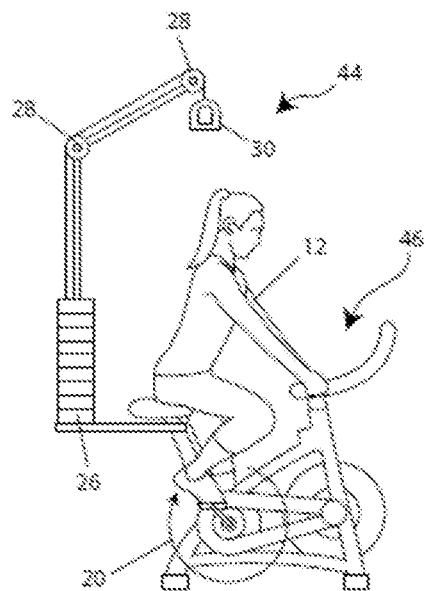
FIG. 9 illustrates a user peddling on a newly designed stationary bike configured with an attached weight training apparatus that has been adjusted from a low position to an overhead position so that the user can engage in pull down weight training during peddling. As envisioned, other cardiovascular equipment such as recumbent stationary bikes, stair steppers, treadmills and elliptical machines are also newly designed to include either the tray embodiment, the attached weight apparatus or both.

FIG. 9 illustrates yet another preferred embodiment of the newly designed stationary bike 46 configured with an adjustable weight training apparatus 44 wherein the weight training apparatus has been adjusted so that the apparatus is situated above the user's head to allow the user to engage in upper body weight training shoulder and arm pulls downs, as well as any other upper body weight training exercises as known in the art. As described, the adjustable weight training apparatus includes a pulley system 28, handles 30, adjustable weight plates 26 and cables that connect the handles to the weight plates. In the illustration, the user is actively peddling 20.

Figure 10:
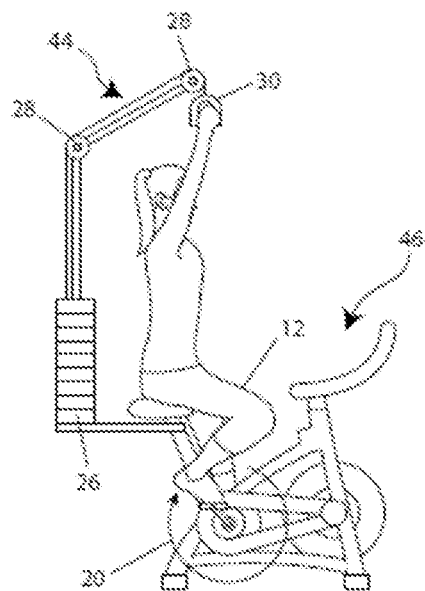
FIG. 10 illustrates a user peddling on the newly designed stationary bike wherein the user is engaging in cardiovascular exercise and weight training simultaneously using an overhead embodiment of the weight training apparatus. The invention includes an adjustable weight training apparatus that can be adjusted by the user to do either overhead weight pulls, or in a lower position wherein the user engages in pull up weight training such as curls.

FIG. 10 illustrates a user 12 actively engaged in both upper body weight training as well as in cardiovascular exercise providing a full body work out. As shown, adjustable weight training apparatus is adjusted so that the weight handles are situated over the user's head 44. In the Figure the user is grasping weight handles 30 which in turn are connected to cables via pulley system 28, the cables being connected to weight plates 26.

Figure 11:
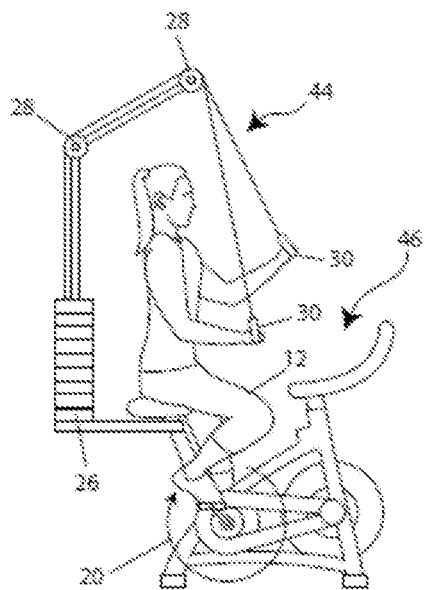
FIG. 11 illustrates the user actively engaged in shoulder pulls downs wherein the user has pulled the weights downward.
Figure 12:
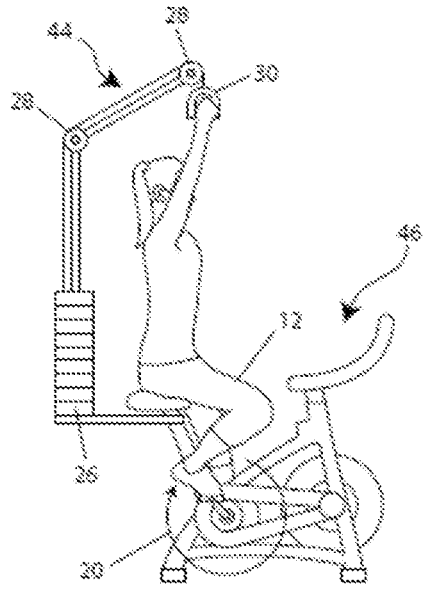
FIG. 12 illustrates the user engaged in shoulder pulls downs wherein the user is allowing the weight handles to return to the upper, starting position.

FIG. 11 illustrates a user 12 actively engaged in both upper body weight training as well as in cardiovascular exercise to provide the user with a full body workout. As shown, the user 12 is in the process of pulling down on weight handles 30 to get an upper body workout in the form of arm or shoulder pull downs. The pulley system 28 and weight plates 26 are engaged with weight cables while the weight training apparatus is adjusted to be over the user's head. FIG. 12 is a continuation of FIG. 11 wherein the user 12 is nearly completed with a pull down exercise and is releasing the weight handle 30 to its original position overhead while maintaining pedaling on the stationary bike.

Figure 13:
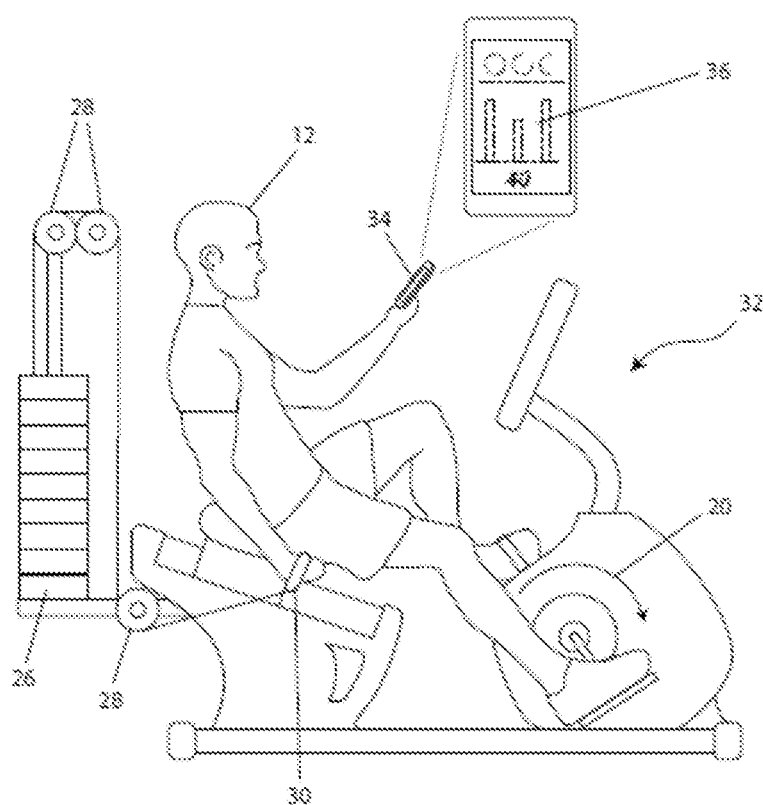
FIG. 13 illustrates yet another preferred embodiment of the invention wherein a newly designed recumbent stationary bike is configured with an adjustable weight training apparatus. Also illustrated is a user actively employing use of an "app" that provides the user with exercise regimens that include various weight training sets combined with a simultaneous cardiovascular routines. For example, the "app" can direct the user to adjust the peddling difficulty to greater difficulty while allowing the user to simultaneously engage in 3 curl sets using the weight training apparatus.

FIG. 13 is an alternative preferred embodiment of the invention that includes a newly designed recumbent stationary bike 32 that includes an adjustable weight training apparatus. The Figure is intended to show that the adjustable weight training apparatus can be configured onto a variety of different pieces of cardiovascular equipment including but not limited to upright and recumbent stationary bikes, elliptical machines, treadmills, stair steppers as well as other equipment as known in the art. The Figure also illustrates the use of an "app" 36 loaded onto a smart device 34 such as a cell or smart phone.

Figure 14:
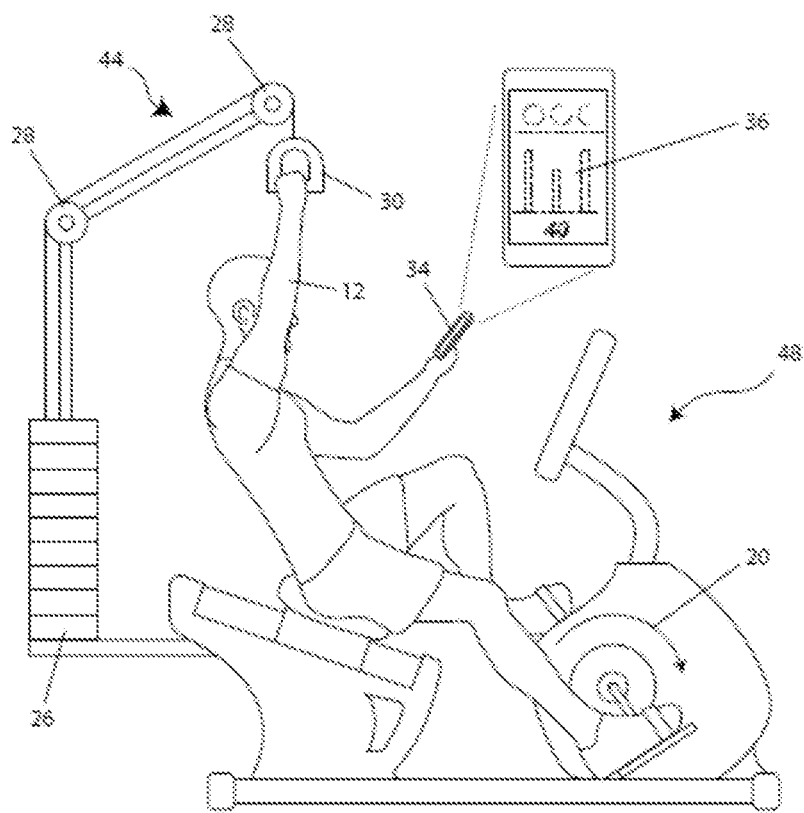
FIG. 14 illustrates a similar embodiment wherein the weight training apparatus has been adjusted to be configured to an overhead position allowing the user to use engage in shoulder and arm pull down exercises. The "app" further provides various routines that allow the user to engage in both cardiovascular exercise as well as weight training exercise simultaneously.

In particular, the user 12 is actively engaged in cardiovascular exercise by pedaling 20 on a recumbent stationary bike that has been configured with an adjustable weight training apparatus that includes a pulley system 28, cables and weight plates 26 that can be modified by a user for the user's appropriate level of weight. As shown, the user is in the process of initiating a weight training set by grasping a weight handle 30 and viewing the invention "app" for an appropriate exercise routine that will provide both a cardiovascular workout as well as an upper body weight training regimen simultaneously. FIG. 14 is a continuation of FIG. 13 wherein the user 12 has nearly completed an upper body weight training set and is in the process of releasing the weight handle 30, via the pulley system 28, cable and weight plates to their original resting positions. The user relies on the "app" of the invention to determine the number of weight training sets in which to engage as well as in the pace of pedaling to be undertaken.

Figure 15:
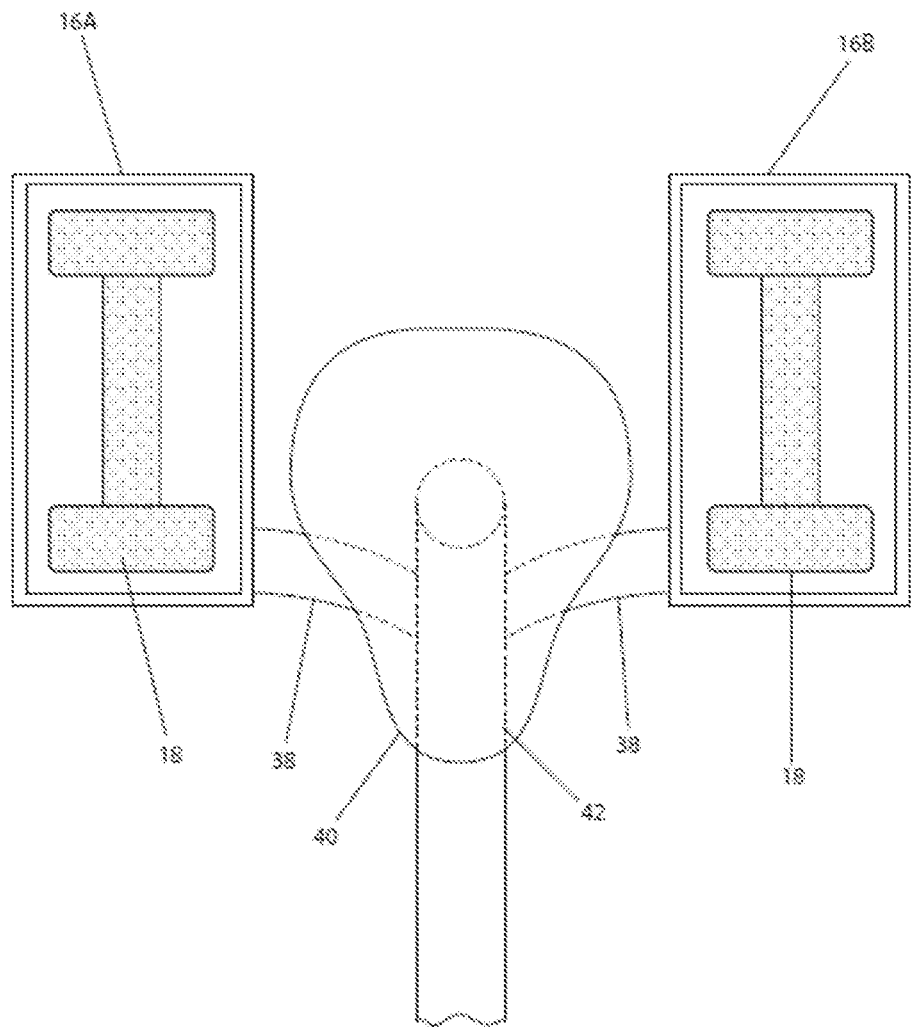
FIG. 15 illustrates a preferred embodiment of the tray apparatus. As shown, weight trays are configured on either side of a bike seat wherein weights are placed during cardiovascular exercise wherein the user is between weight training sets. As envisioned, similar weight tray configurations are included on treadmills, stair steppers, elliptical machines as well as any other type of cardiovascular machine as known in the art.

FIGS. 15 and 16 are close up perspectives of the weight trays of the invention. As shown in FIG. 15, the weight trays 16A and 16B have within them dumb bell free weights 18. The trays in turn are secured on either side of a rider seat 40 with cross bars 38 that connect to the stationary bike. The seat is secured to the stationary bike or other cardiovascular equipment 42. The trays are configured to be within easy reaching distance of a rider on the seat.

FIG. 16 illustrates another close up of the weight tray apparatus wherein the trays comprise a portion of the handle bar 50 of a piece of cardiovascular equipment, such as for example an upright stationary bike. The handle bar includes a video display 52. Weights 18 are placed within the weight trays 16A, 16B so that a user can easily grasp the weights to begin a weight training set, and also so that the user can easily place the weights into the trays during a rest period upon completing a weight training set.

Certain advantages can be obtained in utilizing the present invention. Foremost, the invention provides a full body workout in two primary methods using two primary embodiments. First, in a preferred embodiment the invention provides weight training trays configured and added to a newly designed piece of cardiovascular equipment, wherein the trays hold free weights that are situated either in front of a rider or on either side of a rider, both within easy reach of the rider. The trays allow the rider to engage in weight training sets and to replace the weights into the trays between sets while resting. Cardiovascular exercise is maintained throughout the period of weight training sets and resting in order to maintain a high heart rate and to burn fat.

Next, the method and embodiment of the invention provides a user with a full body workout with newly designed cardiovascular equipment such as an upright or recumbent stationary bike, an elliptical machine, a treadmill, a stair stepper or any other piece of cardiovascular equipment as known in the art that incorporates an adjustable weight training apparatus for a simultaneous upper body and cardiovascular workout. The adjustable weight training apparatus is adjustable so that a user can configure the apparatus to be situated overhead or on either side of the user so that the user can engage in shoulder or arm pull downs, triceps exercise, chest pulls or other weight training exercises of the like and kind. Alternatively, the adjustable weight apparatus can be configured by a user so that the apparatus is situated in a lower position to allow the user to engage in arm curls, shoulder pull ups, chest exercises and other weight training exercises of like and kind.

In both embodiments, the user can engage in weight training sets in which the user either follows the direction of an "app" or devises a weight training scheme independently to engage in weight training sets in which the user lifts weights for 10 or more repetitions for several sets while pedaling, walking, running, stair stepping or engaging in an elliptical workout. In between sets the user can place their free weights into the weight trays, or alternatively, with the adjustable weight apparatus can simply allow the weight plates to return to their original position by releasing the weight handles of the invention. During weight training rest periods, the user continues to peddle, walk, run, stair step or engage in elliptical exercise in order to maintain a higher heart rate and to burn fat at a greater rate.

Although the invention has been described with reference to the above examples, it will be understood that modifications and variations are encompassed within the spirit and scope of the invention. Accordingly, the invention is limited only by the following claims.

What is claimed is:

1. An exercise system to provide a full body cardiovascular and upper body work out comprising:
   at least one piece of adjustable weight training apparatus;
   a mountable cardiovascular machine;
   wherein the at least one piece of adjustable weight training machine is configured with and directly connected to the mountable cardiovascular machine;
   wherein the adjustable weight training apparatus comprises, support equipment, resistance cables, cable pulleys, weight handles and weight plates wherein the weight training apparatus is adjusted by a user whom has mounted the mountable cardiovascular machine;
   wherein the user adjusts the amount of weight the user desires to undertake in upper body exercise by selecting the number of weight plates the user desires;
   wherein the adjustable weight training apparatus is adjusted by the user so that the apparatus is positioned over the user's head, at a midway position or in a lowered position;
   wherein the exercise system apparatus further comprises weight trays designed to hold at least two free weights;
   wherein the weight trays are configured in the front section of the mountable cardiovascular machine in front of the user within reach of the user;
   wherein weight trays are also attached to the mountable cardiovascular machine and positioned on both sides of the user within reach of the user;
   wherein the exercise system further comprises an "app" uploaded onto a smart or mobile device;
   wherein the "app" provides the user with a rate that the user engages in cardiovascular exercise and also directs the user as to the upper body exercises to be undertaken using the adjustable weight training apparatus;
   wherein the user engages in cardiovascular exercise while simultaneously engaging in upper body weight training thereby engaging in a full body workout including both cardiovascular and upper body exercises.

2. The exercise system of claim 1 wherein the user engages in arm and shoulder pull down exercises at times when the adjustable weight training apparatus is positioned over the user's head.

3. The exercise system of claim 1 wherein the user engages in pectoral and chest exercises at times when the adjustable weight training apparatus is positioned at the midway position.

4. The exercise system of claim 1 wherein the user engages in arm pull up exercises at times when the adjustable weight training apparatus is positioned in a lowered position.

5. The exercise system of claim 1 wherein the mountable cardiovascular machine comprises an upright stationary bike.

6. The exercise system of claim 1 wherein the mountable cardiovascular machine comprises a recumbent stationary bike.

7. The exercise system of claim 1 wherein the mountable cardiovascular machine comprises a treadmill.

8. The exercise system of claim 1 wherein the mountable cardiovascular machine comprises an elliptical machine.

9. The exercises system of claim 1 wherein the trays configured in front of the user comprise a front panel or handle bar of the mountable cardiovascular machine.

10. A method of providing a user with a full body workout wherein the method comprises the user engaging in cardiovascular exercise simultaneously with upper body exercise;
    wherein the user engages a mountable cardiovascular machine wherein the mountable cardiovascular machine is configured with and directly connected to at least one piece of adjustable weight training apparatus;
    wherein the adjustable weight training apparatus comprises resistance cables, cable pulleys, support equipment, weight handles and weight plates that are adjusted by a user whom has mounted the mountable cardiovascular machine;
    wherein the user adjusts the amount of weight the user desires to undertake in upper body exercise by selecting the number of weight plates the user desires;
    wherein the user adjusts the adjustable weight training apparatus so that the apparatus is situated over the user's head, at a midway position or in a lowered position;
    wherein the exercise system apparatus further comprises weight trays designed to hold at least two free weights;
    wherein the weight trays are configured in the front section of the mountable cardiovascular machine in front of the user within reach of the user;
    wherein weight trays are also attached to the mountable cardiovascular machine and positioned on both sides of the user within reach of the user;
    wherein the exercise system further comprises an "app" uploaded onto a smart or mobile device;
    wherein the "app" provides the user with a rate that the user engages in cardiovascular exercise and also directs the user as to the upper body exercises to be undertaken using the adjustable weight training apparatus;
    wherein the user engages in cardiovascular exercise while simultaneously engaging in upper body weight training thereby engaging in a full body workout including both cardiovascular and upper body exercises.

11. The method of claim 10 wherein the user engages in arm and shoulder pull down exercises at times when the adjustable weight training apparatus is positioned over the user's head.

12. The method of claim 10 wherein the user engages in pectoral and chest exercises at times when the adjustable weight training apparatus is positioned at the midway position.

13. The method of claim of claim 10 wherein the user engages in arm pull up exercises at times when the adjustable weight training apparatus is positioned in a lowered position.

14. The method of claim 10 wherein the mountable cardiovascular machine comprises an upright stationary bike.

15. The method of claim 10 wherein the mountable cardiovascular machine comprises a recumbent stationary bike.

16. The method of claim 10 wherein the mountable cardiovascular machine comprises a treadmill.

17. The method of claim 10 wherein the mountable cardiovascular machine comprises an elliptical machine.

18. The method of claim 10 wherein the trays configured in front of the user comprise a front panel or handle bar of the mountable cardiovascular machine.

19. The method of claim 10 wherein the user performs various upper exercises by lifting the free weights.

20. The method of claim 19 wherein the user continuously exercises the user's lower body by engaging the mountable cardiovascular machine during periods of time when the user is not conducting upper body exercises with the free weights, the free weights being placed in the weight trays.

\* \* \* \* \*